(12) United States Patent
Dodgson et al.

(10) Patent No.: US 6,558,519 B1
(45) Date of Patent: *May 6, 2003

(54) GAS SENSORS

(75) Inventors: John Robert Dodgson, Croydon (GB); Malcolm Trayton Austen, Hayes (GB); Ian Robins, Hillingdon (GB)

(73) Assignee: Central Research Laboratories Limited, Hayes (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/319,446
(22) PCT Filed: Dec. 5, 1997
(86) PCT No.: PCT/GB97/03377
§ 371 (c)(1),
(2), (4) Date: Jul. 27, 1999
(87) PCT Pub. No.: WO98/25139
PCT Pub. Date: Jun. 11, 1998

(30) Foreign Application Priority Data

Dec. 7, 1996 (GB) ............................................. 9625463

(51) Int. Cl.[7] ...................... G01N 27/26; G01N 27/404
(52) U.S. Cl. ...................... 204/401; 204/412; 204/415
(58) Field of Search ................ 204/401, 415, 204/412

(56) References Cited

U.S. PATENT DOCUMENTS

| | | | | |
|---|---|---|---|---|
| 5,092,980 A | * | 3/1992 | Maurer et al. | 204/415 |
| 5,098,547 A | * | 3/1992 | Bryan et al. | 204/401 |
| 5,273,640 A | * | 12/1993 | Kusanagi et al. | 204/401 |
| 5,405,512 A | * | 4/1995 | Parker | 204/401 |
| 5,650,062 A | * | 7/1997 | Ikeda et al. | 204/415 |
| 5,830,337 A | * | 11/1998 | Xu | |

FOREIGN PATENT DOCUMENTS

| | | | |
|---|---|---|---|
| EP | 0744620 A1 | * | 11/1996 |
| GB | 1552538 | * | 9/1979 |
| GB | 2254696 A | * | 10/1992 |
| WO | WO 96/14576 | * | 5/1996 |

* cited by examiner

Primary Examiner—T. Tung
(74) Attorney, Agent, or Firm—William H. Bollman

(57) ABSTRACT

A gas sensor including a housing containing at least a sensing electrode, a counter electrode, a test electrode, and electrolyte means in contact with such electrodes. The housing permits gas from the environment to flow to the sensing electrode. The gas sensor is operable either in a normal mode of operation in which potentials are applied to the electrodes for detecting when a gas to be sensed is present at the sensing electrode, or in a test mode of operation in which potentials are applied to the electrodes so that the test electrode generates a gas which flows to the sensing electrode to enable an indication whether the sensor is operating correctly.

16 Claims, 6 Drawing Sheets

GAS SENSORS

This invention relates to gas sensors with a capability for self-testing.

Conventional electrochemical gas sensors operate by oxidising the gas at a sensing electrode, thereby generating a current. The rate of access to the electrode is determined by a diffusion barrier, and the rate at which the electrode can oxidise the gas is arranged to be very much greater than the rate at which gas diffuses through the barrier. Therefore the rate of oxidation, and hence the current, is controlled solely by diffusion, and this is a known value (for a given gas concentration) when the sensor is manufactured. If the activity of the electrode falls with time e.g. through poisoning, then the current eventually becomes limited by the lowered oxidation rate at the electrode and the sensitivity of the sensor falls. The sensor does not fail safe—there is no way of telling from the cell output whether the gas concentration is low, or the concentration is higher and the electrode has lost activity.

Reliability of such sensors is ascertained by regular tests involving exposure to a calibration gas. In many situations, for example in a domestic CO safety monitor, this is undesirable. A sensor with a self test function, either triggered remotely or locally, would be highly advantageous.

GB-A-1,552,538 describes a self-test sensor assembly consisting of two parts, a sensor and a gas generation means, for example an electrolysis cell, joined by a delivery channel. Test gas is delivered directly to the sensing electrode of the sensor, with a membrane between the point of gas delivery and the outside world. Delivery is by a piston, a pressure difference resulting from the generation of gas itself, or other means. Signal gas enters the sensor from the atmosphere via the membrane. In this arrangement the concentration of test gas seen by the sensing electrode depends on the balance of the rate of generation of the gas and the rate of loss through the membrane—the latter depends on the conditions (air flow) outside the membrane. As the generator is remote from the sensing electrode, there is a large volume to be filled with gas in order to ensure that a consistent known concentration is reached. This means the design is likely to require significant power, which is a limitation of the use of such a principle in a low power domestic monitor circuit.

GB-A-2245711 (corresponding U.S. Pat. No. 5,273,640 Kusanagi et al) describes a gas sensor with solid electrolyte layers disposed on two sets of electrodes, one designed for a gas sensing function, and the other set provided for a test function. The test function electrodes are arranged to sense a gas normally present in the atmosphere, e.g. oxygen. A decrease in the signal from the test electrode is taken to indicate a either a decrease in activity of the test electrodes, or a decrease in the permeability of the solid electrolyte, through which test and signal gas must pass before they reach the electrodes. Such change in permeability is a major factor in the performance of the sensor type disclosed in GB-A-2245711. The test of electrode decay rests on the assumption that the test electrodes will decay in the same way as the sensing electrodes. The test reaction using $O_2$ is fundamentally different from the sensing reaction for oxidisable gases, being a reduction rather than an oxidation reaction, and so this form of test is likely to prove unreliable. A test where the sensing electrode oxidises test gas generated in known quantity, as in GB-A-1,552,538 would be advantageous.

The present invention provides a gas sensor including a housing containing at least a sensing electrode, a counter electrode, a test electrode, and electrolyte means in contact with such electrodes, the housing permitting gas from the environment to flow to the sensing electrode, and the gas sensor being such as to be operable either in a normal mode of operation in which potentials are applied to the electrodes for detecting when a gas to be sensed is present at the sensing electrode, or in a test mode of operation in which potentials are applied to the electrodes so that the test electrode generates a gas which flows to the sensing electrode to enable an indication whether the sensor is operating correctly.

Thus in accordance with the invention a cheap and accurate means is provided of self-testing, wherein the test gas is generated internally of the sensor and in a controlled amount by application of a suitable voltage potential.

A gas sensor according to claim 1 comprising of a planar arrangement of one or more sensing electrodes and one or more electrolytic generation electrodes on a common substrate in contact with common or separate electrolytes with associated counter and reference electrodes as may be required, such that the generation electrodes are close to the sensing electrodes, so as to minimise the amount of gas that is needed to effect the test. The gas might be delivered to the sensing electrode in the gas phase, by evolution into a communicating space above the electrodes, and access from generating to sensing electrodes might be via a diffusion barrier. The gas might alternatively be delivered to the sensing electrode in solution. The latter will give a measure of electrode activity different from, but related to, the activity measured for gas phase reaction, but will still give an indication of performance.

In a preferred embodiment, the planar arrangement of generating and sensing electrodes gives close proximity and small generated volume—hence low power and fast response. More than one generating electrode may be placed around the sensing or sensing electrode to further improve fast response and further reduce power requirements. An interleaved array of generating and sensing electrodes may also be employed. As preferred, screen printed electrodes and assembly method as described in our copending application WO 96/14576 (ref. PQ 12,622) is employed, that is: providing electrodes as porous planar elements on a substrate, a housing containing an electrolyte reservoir, and electrical terminals; positioning the substrate relative to the housing so that a portion of an electrode is positioned adjacent an electrical terminal; and bonding the substrate to the housing so that the electrode is electrically connected with the electrical terminal means while the porosity of the electrode is blocked in the region of the electrical connection to prevent permeation of electrolyte to the electrical connection. The electrodes are preferably formed of a porous electrically conductive material containing PTFE or similar polymeric binder, preferably particles of catalyst, and optional additional catalyst support material and material to enhance conductivity. The electrodes might be deposited onto the substrate by for example screen printing, filtering in selected areas from a suspension placed onto the substrate, by spray coating, or any other method suitable for producing a patterned deposition of solid material. Deposition might be of a single material or of more than one material sequentially in layers, so as for example to vary the properties of the electrode material through its thickness or to add a second layer of increased electrical conductivity above or below the layer which is the main site of gas reaction. The preferred metal deposit is platinum or platinum; carbon, although other deposits may be employed such as carbon or ruthenium dioxide.

The generator electrode may be placed close to the diffusion barrier inlet for signal gas, so that in self-test, some gas is lost to the outside and some is oxidised by the sensing electrode. If the diffusion barrier becomes blocked, the concentration seen by the sensing electrode during self-test is higher than would be the case without blockage, thus providing a means of checking whether the diffusion barrier is blocked. The accuracy of this check can be improved by delivering the test gas between two diffusion barriers.

Two levels of test may be provided: (1) a quick check of sensor function by generating gas in solution, which then diffuses to the sensing electrode through the solution—this uses low power; and (2) a check on diffusion barrier blockage, which might also give a calibration of the sensor, in which gas is delivered to the sensing electrode in the gas phase as above. The cell may be provided with two generating electrodes—a submerged electrode without access to the gas phase for the first test, and an electrode on a porous substrate communicating with the gas phase for the second.

An actuator may be incorporated into the cell to close the diffusion barrier during self test. This would remove the effect of air currents on the test result. Comparison of open and closed responses test for blockage of the barrier—if there is no blockage, the closed response will be greater than the open response.

BRIEF DESCRIPTION OF THE DRAWINGS

Preferred embodiments of the invention will now be described with reference to the accompanying drawings, in which.

DESCRIPTION OF THE PREFERRED EMBODIMENTS

Figure 1:
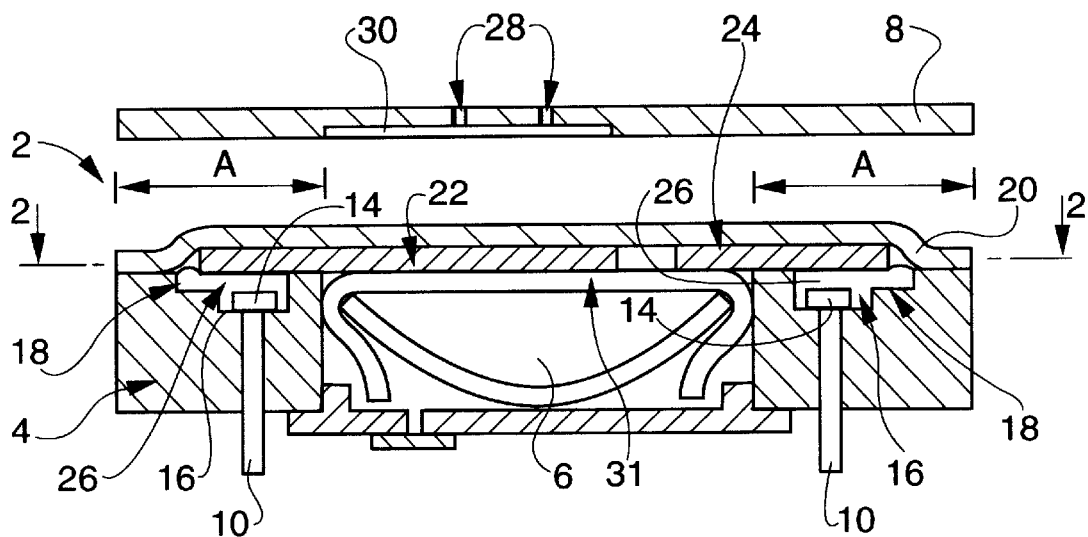
FIG. 1 is a cross-section through a circular gas sensor as employed in the embodiments of the invention.

Referring now to FIG. 1, this shows a construction of gas sensor employed in the embodiments of the invention described below. A gas sensor comprises an electrochemical gas sensor 2 comprising a two part housing, namely a body part 4 which is cylindrical with a hollow interior 6 for forming a electrolyte reservoir, and a disc-shaped cap member 8. Electrical terminal pins 10 of nickel or tinned copper, have heads 14 thereon located in recesses 16 in the top of housing body 4. A porous flexible substrate 20, in the form of a disc, is disposed on the upper surface of body member 4. Electrodes 22, 24 formed of a mixture of electrically conductive catalyst particles in PTFE binder, are screen printed or filter deposited onto the lower surface of the substrate in the form of segments. A small amount of conductive polymer/carbon composite 26 is placed in recesses 16 over each contact pin head 14. The cap member 8 has through holes 28 drilled therein to a recessed manifold area 30 for permitting atmospheric gas to diffuse through apertures 28 and thence, via manifold area 30, through substrate 20 to electrode 22. Electrolyte within electrolyte recess or reservoir 6 is maintained in contact with electrodes 22, 24 by means of a wick arrangement 31. To assemble the structure shown in FIG. 1, the base part 4 has electrical terminal contact pins 10 positioned therein with conductive polymer or composite 26 positioned within the recesses 16 over the heads 14. The substrate is positioned over the top of the cylindrical body 4. Heat and pressure is applied in the areas A as shown by means of a press tool (not shown) in order to compress the substrate 20 and the electrodes 22, 24 onto the upper plastic surface of housing 4 and the conductive polymer or composite 26 in order to bond the assembly together so that the substrate 20 is securely fixed to the top of the housing 4. The compression of the electrodes 22, 24 and the substrate 20 in the area A, together with the impregnation into the porous substrate 20 of the plastic housing and the conductive polymer or composite 26, ensure that the substrate 20 and electrodes 22,24 are sealed to prevent the ingression of electrolyte into the regions of the electrical connections. Simultaneously, the plastic mass 26 moulds itself around the heads 14 of the terminal pins 10, thereby assuring a good electrical connection between the contact pins and the electrodes 22,24.

In the embodiments described below, an aqueous electrolyte is employed, generating $H_2$ as the test gas. $O_2$ is produced at counter electrodes 24 in the electrolytic circuit. The generator cell with separate electrolyte in FIG. 5 may use an electrolyte different from that of the sensor in order to generate a specific gas, for example a mixture of potassium bisulphate, sulphur and water for electrolytic generation of $H_2S$.

Figure 2:
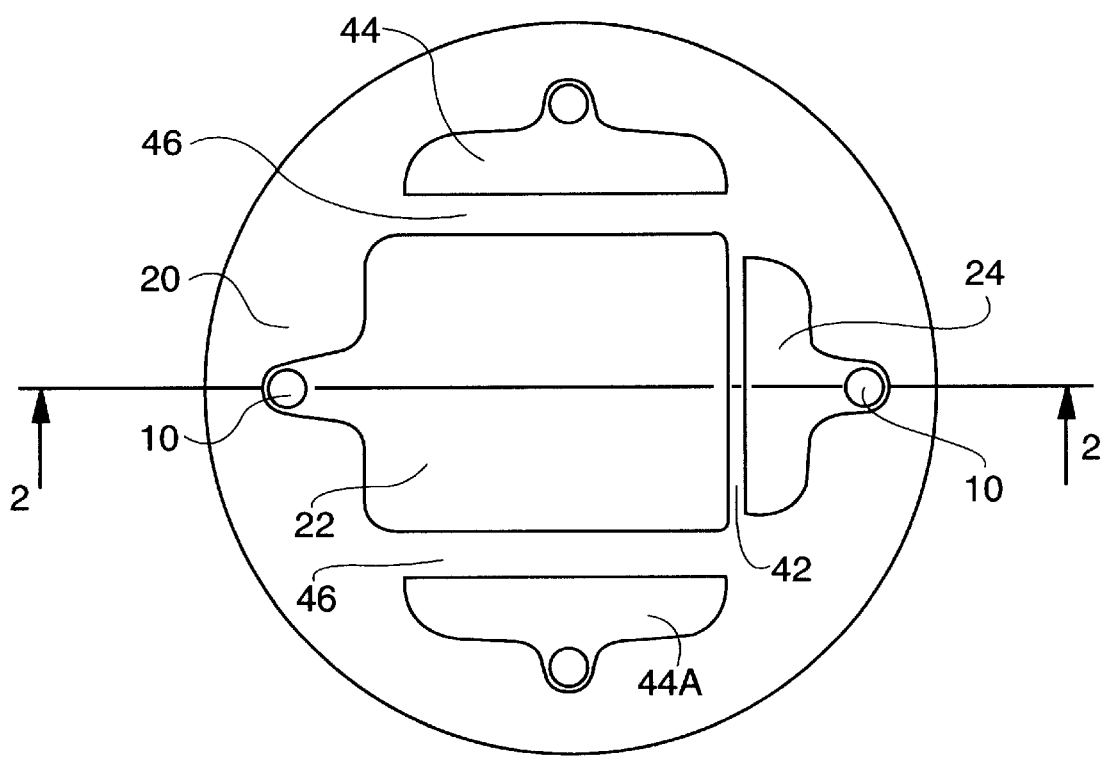
FIG. 2 is a plan view of the electrode configuration of the first embodiment of the invention.
Figure 2A:
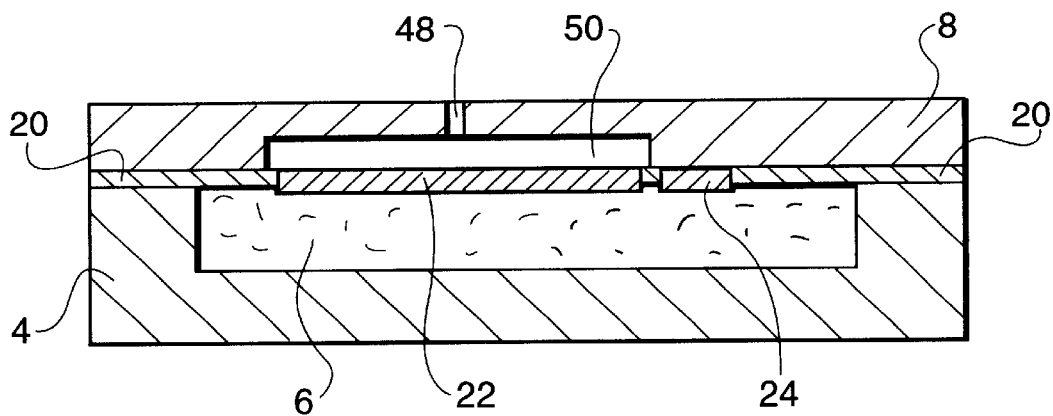
FIG. 2A is a partial sectional view along the line 2—2 of FIG. 2 to which a cap member has been added.

Referring now to FIG. 2, this shows an electrode configuration of a first embodiment of the invention which may be employed with the structure of FIG. 1. In FIG. 2 similar parts to those shown in FIG. 1 are denoted by the same reference numeral. A sensing or sensing electrode 22 occupies the central region of substrate 20 and is coupled at its left hand end (as viewed in FIG. 2) to a contact pin 10. A test electrode 24 is separated from the sensing electrode 22 by a narrow channel 42 and connected at its right hand end to an electrical contact pin 10. As shown in FIG. 2, two counter electrodes 44 and 44A are shown in two regions adjacent sensing electrode 22 on the same side of the substrate 20 as the electrode 22 and are electrically separated by narrow channels 46. As shown in FIG. 2A, the cap member 8 has a single aperture 48 providing a diffusion barrier to a manifold recess 50, which is dimensioned so the edge of the recess is located above channel 42. The reservoir 6 in the body 4 contains a common aqueous electrolyte in contact with all the electrodes 22, 24, 44, 44A.

In operation, gas from the environment diffuses through aperture 48 to manifold 50. If the air contains a gas to be sensed, for example, CO, an electrochemical reaction is created within electrode 22, an electrochemical reaction is created at the counter electrode 44 with $O_2$ in the atmosphere, and current is carried through the electrolyte by ions produced in the reactions and by electrons in an external circuit such as that shown in FIG. 6A. The current in the external circuit indicates the CO concentration in the atmosphere. Additionally, a reference electrode might be provided adjacent to the sensing electrode 22, and the reference electrode 61, counter electrode 44 and sensing electrode 22 operated using a potentiostat circuit as in FIG. 6B, such circuits being well known in the art.

Figure 6A:
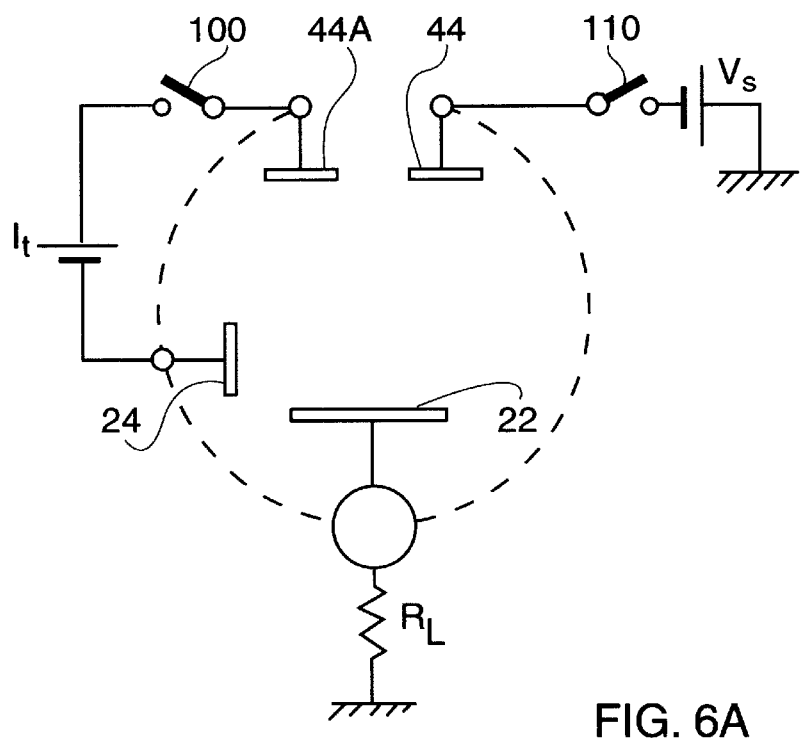
FIGS. 6A, 6B and 6C are schematic circuit diagrams of a circuit for energising the electrodes of the above embodiments.

In order to test whether the gas sensor of FIG. 2 is operating correctly, the switch 100 in FIG. 6A is employed to apply an electrical potential between electrodes 24 and 44A and thereby activate test electrode 24 in order to generate hydrogen gas, $H_2$. This gas migrates across channel 42, through the electrolyte in reservoir 6, as indicated in FIG. 2A, to the sensing electrode 22 where it creates a desired electrochemical reaction in order to produce, in the circuit of FIGS. 6A or 6B, a current indicative of the $H_2$ generated if the circuit is operating correctly. $O_2$ is generated at the second counter electrode 44A to complete the gas generation circuit.

Figure 2B:
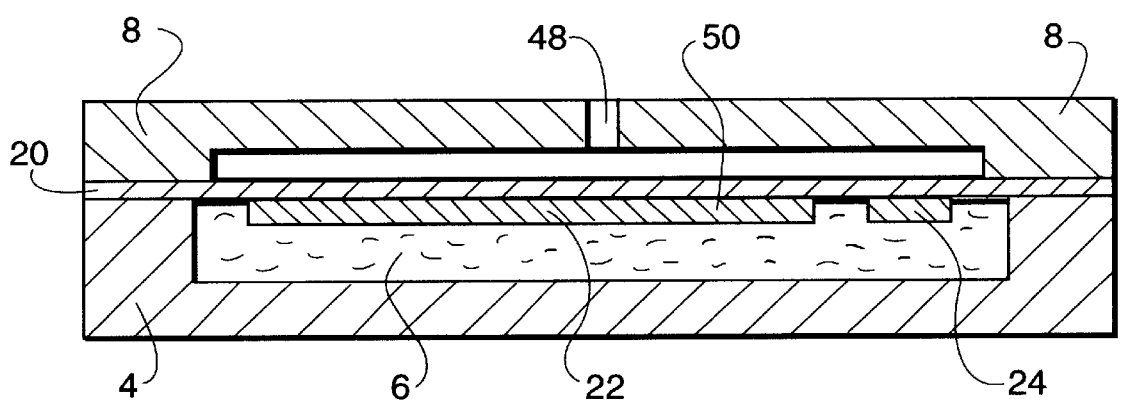
FIG. 2B is an alternative partial sectional view along the line 2—2 of FIG. 2 to which a different cap member has been added.

The description above describes test gas moving from the generating electrode 24 to the sensing electrode 22 through the electrolyte. FIG. 2B shows an alternative embodiment to that shown in FIG. 2A. The manifold recess area 50 is dimensioned such that the generating and sensing electrodes 24,22 respectively share a communicating gas space, allowing test gas to pass from the generating electrode 24 to the sensing electrode 22 in the gas phase. This will allow higher concentrations of test gas to be delivered.

Figure 6B:
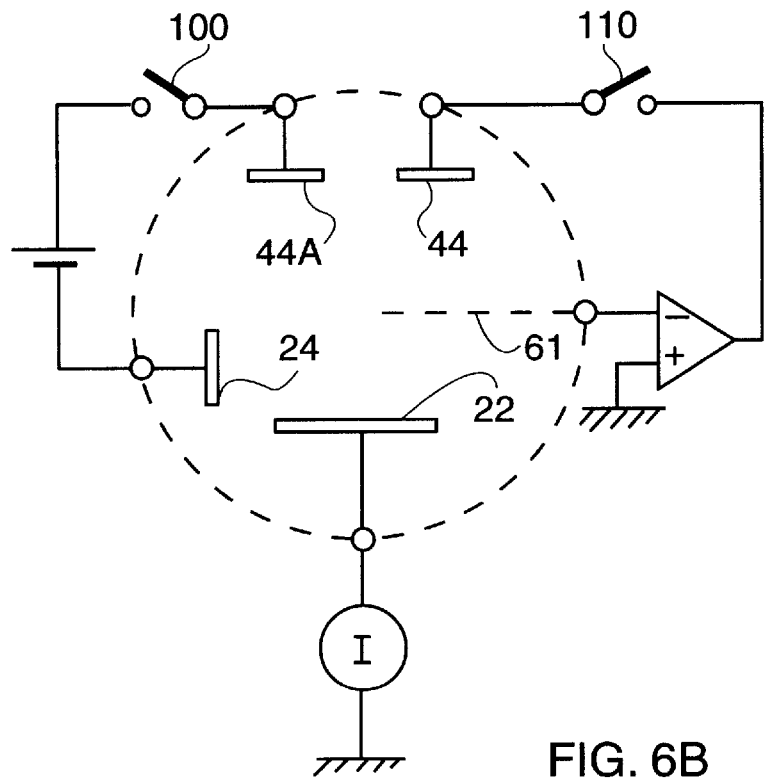
Figure 6C:
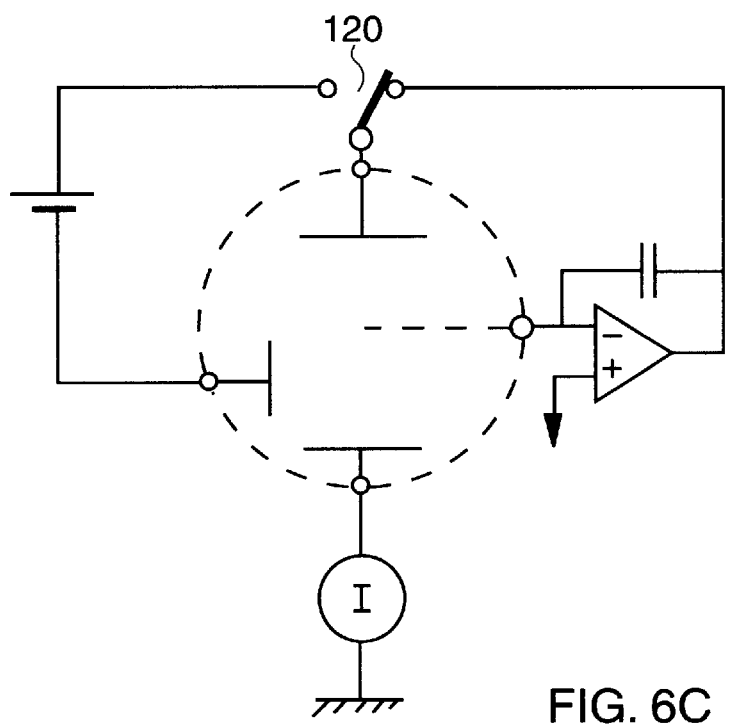

As a further possibility, there may be only a electrode sensing(22), reference electrode, test electrode 24 , and a single counter electrode 44 or 44A, and the cell operated with a circuit such as in FIG. 6C. In this case, the operation of the sensor will be adversely affected by generation of test gas, and so a changeover switch 120 is provided which has a position in which the cell senses gas, and a second position in which the cell generates test gas. In self-test, test gas is generated for a time, building up a concentration of gas in either the electrolyte in the vicinity of the sensing electrode 22, or a gas space above it. The switch 120 is then moved to the sense position, and the buildup of test gas is sensed.

Figure 3:
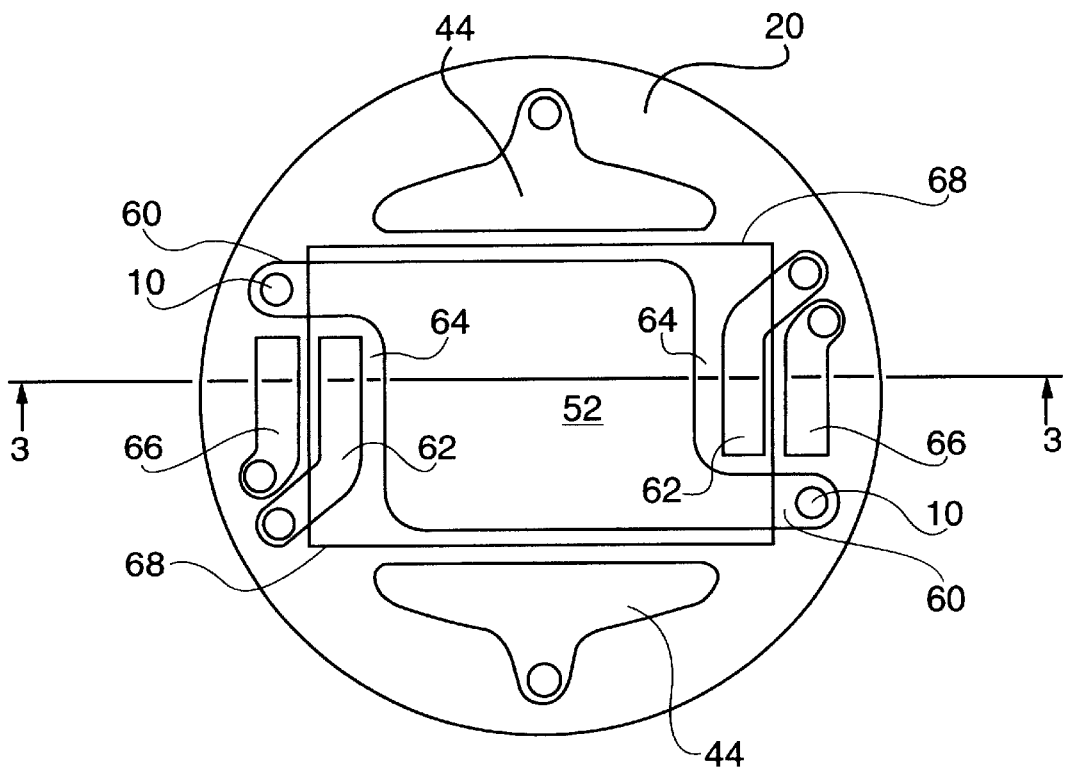
FIG. 3 is a plan view of the electrode configuration for a second embodiment of the invention.
Figure 3A:
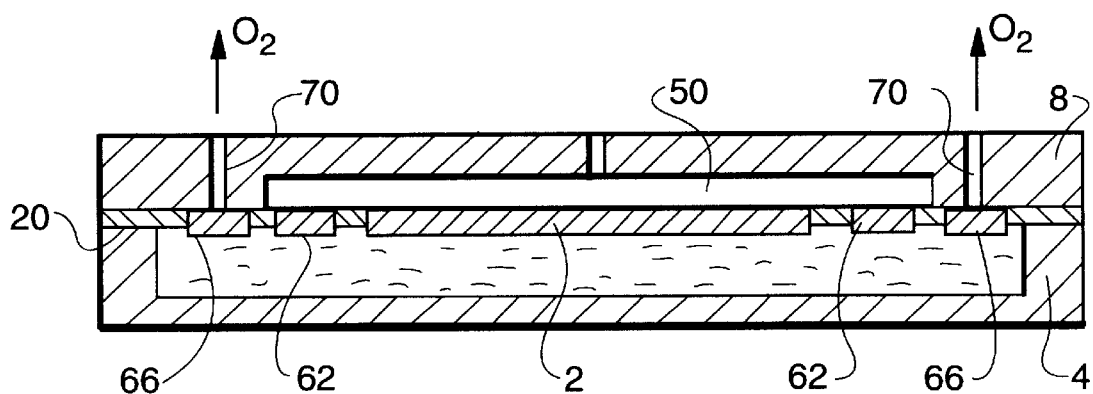
FIG. 3A is a sectional view along the line 3—3 to which a cap member has been added.

Referring now to FIGS. 3 and 3A, these show a modified electrode configuration from that of FIG. 2, wherein main sensing electrode 52 is generally rectangular in form but having two projecting portions 60 at diagonally opposite corners for connection to contact pins 10. Counter electrodes 44 are provided adjacent the upper and lower sides of the electrode 52. On the lateral sides of electrode 52 are disposed first and second test electrodes 62 separated from electrode 52 by narrow channels 64. In addition, third and fourth counter electrodes 66 are provided, for developing $O_2$ gas during testing, in strip form and separated from electrodes 62 by narrow channels 68. As may be seen from FIG. 3A, test electrodes 64 for generating $H_2$ are disposed beneath manifold area 50, allowing $H_2$ to flow on test through the manifold to the sensing electrode, whereas $O_2$ generating counter electrodes 66 are closed off from the manifold and communicate with the environment by apertures 70 for releasing $O_2$ gas.

Figure 4:
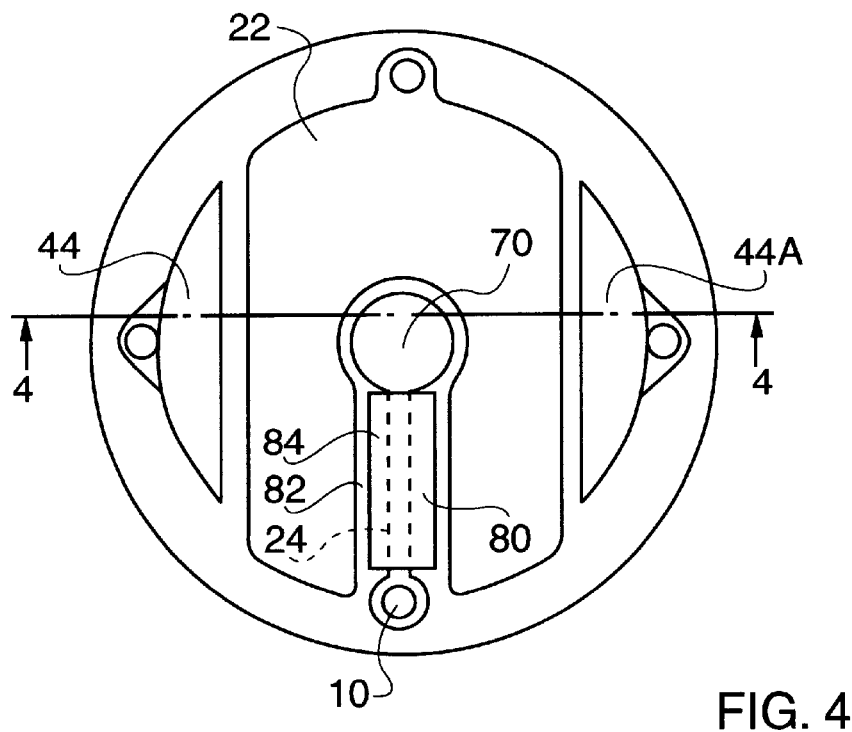
FIG. 4 is a plan view of the electrode configuration of a third embodiment of the invention.
Figure 4A:
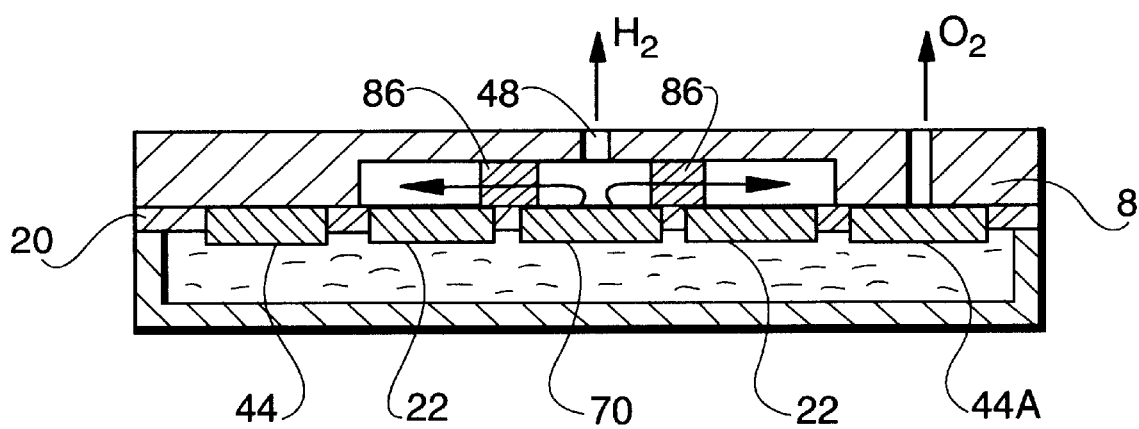
FIG. 4A is a sectional view along the line 4—4.

Referring now to FIGS. 4 and 4A, a further configuration of electrodes is shown, somewhat similar to FIG. 2 but wherein a test electrode 70 for generating $H_2$ gas is disposed in the centre of the sensing electrode 22 and with a track 80 leading to electrical contact pin 10. A narrow U-shaped channel 82 separates the electrodes and an underlayer 84 separates track 80 from the electrolyte so that reaction only occurs at the electrode 70. The underlayer could be achieved by overprinting or heat laminating over the top of the electrode track 70. As shown in FIG. 4A, manifold recess encompasses the sensing electrode 22 and $H_2$ generating electrode 24, but not counter electrodes 44. A diffusion barrier comprising a porous annular member 86 surrounds the gap 82 between the $H_2$ generating electrode and the sensing electrode. In this embodiment, in the test mode, $H_2$ gas developed by electrode 70 permeates through manifold 50 via diffusion barrier 86. The $H_2$ generator electrode 70 is placed closer to the diffusion barrier 86 than is the sensing electrode 22. This allows part of the $H_2$ to escape through the barrier 86 in test mode. The proportion that escapes is controlled by the permeability of the diffusion barrier 86 and the dimensions of the aperture 48 in the cap 8. The response from the sensing electrode 22 in test mode will depend on the ratio of $H_2$ escaping to that oxidised at the sensing electrode 22. If the electrode 22 decays, the test response will fall below a pre-determined value. If the diffusion barrier 86 becomes blocked, e.g. by dust from the atmosphere, $H_2$ will no longer escape and the test response will exceed the value, giving warning of blockage.

Figure 5:
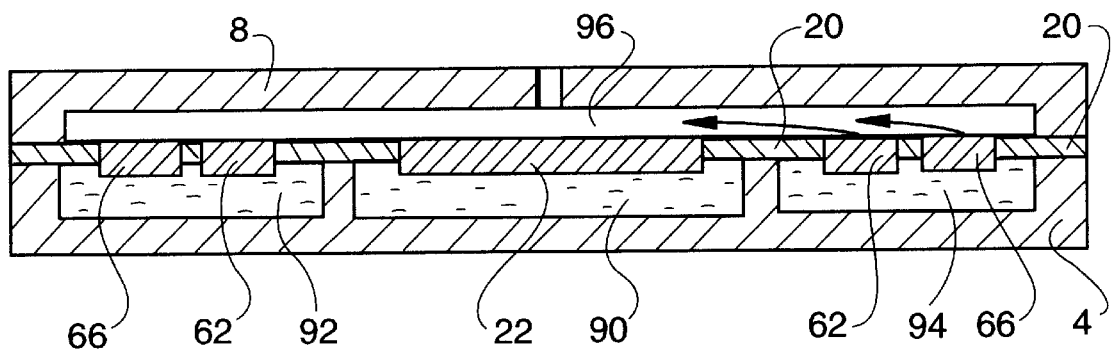
FIG. 5 is a sectional view of a fourth embodiment of the invention, with separate electrolyte reservoirs.

Referring now to FIG. 5, this is a cross sectional view of a further embodiment employing an electrode configuration as shown in FIG. 3, but having a modified electrolyte reservoir construction and manifold construction. As shown, three separate electrolyte reservoirs 90, 92, 94 are provided, reservoir 90 containing an aqueous electrolyte for ensuring normal operation of sensing electrode 22, and reservoirs 92, 94 containing electrolyte for generating $O_2$ and $H_2$ during the test phase. As shown, the enlarged manifold area 96 permits both $H_2$ and $O_2$ to flow through the manifold area to the sensing electrode 22. This embodiment may be used if it is found that the electrolysis current passing through the common sensing and generation electrolyte in the examples above, disturbs the sensor operation excessively. More than two gas generating cells may be included as required to give fast response, or only one to give low power consumption.

In the above embodiments, an actuator-driven valve may be incorporated in the diffusion barrier to close off the barrier during-part of the test cycle, so preventing $H_2$ being lost to the atmosphere. If the diffusion barrier is blocked then there will be no increase in concentration when the valve is closed and this can then be detected. The system might also be used to prevent the influence on the test, of variable loss of $H_2$ owing to air currents, by closing the valve throughout the self-test process.

Referring to FIGS. 6A, 6B, 6C, these show a circuit suitable for actuation of the above embodiments. In FIG. 6A, a sensing electrode 22 is coupled in a circuit with a counter electrode 44 with a switch 110 and a source of potential Vs. A test electrode T is coupled in a further circuit with counter electrode 44A, switch 100 and a source of potential Vt. As discussed above all the electrodes are either in contact with a common electrolyte, or with separate electrolytes for the sensing and generation circuits. In operation, switch 110 is closed to allow sensing, and switch 100 closed intermittently to enable test operation. In FIG. 6B, the sensing cell is provided with a reference electrode as well as the sensing and counter electrodes, and operated by a potentiostat circuit. Switch 110 is closed to enable sensing operation as before, and switch 100 closed intermittently to enable test operation. Switch 110 may be opened while switch 100 is closed, if test gas generation interferes with normal sensing operation of the cell. In FIG. 6C, a single counter electrode 49 is provided, and all electrodes are in contact with a common electrolyte. In this case, a changeover switch 120 is provided, which in one position enables sensing operation, and in the other, generates test gas which accumulates in the vicinity of the sensing electrode. The switch is then moved back to the sensing position, the test gas is reacted, and the test function carried out.

What is claimed is:

1. A gas sensor, comprising:
 a housing having disposed therein:
  at least one sensing electrode;
  at least one counter electrode;
  at least one test electrode; and
  at least one electrolyte in contact with at least one of said at least one sensing electrode, said at least one counter electrode and said at least one test electrode;
 wherein said housing permits at least a gas to be sensed to flow from an environment to said at least one sensing electrode;
 wherein said gas sensor is operable in a normal mode of operation in which said gas sensor detects whether said gas to be sensed is present at said at least one sensing electrode, and in a test mode of operation in which said at least one test electrode generates a test gas which flows to said at least one sensing electrode to enable an indication whether said gas sensor is operating correctly;
 wherein at least two of said at least one sensing electrode, said at least one counter electrode and said at least one test electrode are mounted side-by-side on a same side of a common porous gas permeable substrate to define a planar electrode assembly; and
 wherein said at least one sensing electrode and said at least one test electrode are mounted side-by-side on the same side of said common porous gas permeable substrate and are in contact with a common electrolyte.

2. The gas sensor according to claim 1, further comprising:
 at least one reference electrode,
 wherein said at least one counter electrode, said at least one reference electrode, said at least one sensing electrode and said at least one test electrode are mounted side-by-side on the same side of said common porous gas permeable substrate, and are in contact with a common electrolyte.

3. The gas sensor according to claim 1, wherein:
 said at least one test electrode is arranged and positioned relative to said at least one sensing electrode so that gas generated by said at least one test electrode is released into a communicating space in the vicinity of said at least one sensing electrode.

4. The gas sensor according to claim 1, further comprising:
 a diffusion barrier through which gas generated by said at least one test electrode diffuses to reach said at least one sensing electrode.

5. The gas sensor according to claim 1, wherein:
 said common porous gas permeable substrate is a flexible gas permeable membrane that is impermeable to electrolytes.

6. The gas sensor according to claim 1, wherein:
 said sensing electrode occupies a central region of said common porous gas permeable substrate, said at least one test electrode being separated from said at least one sensing electrode by a narrow first channel, and
 wherein said at least one counter electrode is located adjacent said at least one sensing electrode and is electrically separated from said sensing electrode by at least a second channel.

7. The gas sensor according to claim 1, wherein:
 said housing comprises:
  a cap having a diffusion hole communicating with a manifold recess adjacent said at least one sensing electrode, an edge of said manifold recess being located between said at least one sensing electrode and said at least one test electrode.

8. The gas sensor according to claim 1, wherein:
 said at least one sensing electrode is generally rectangular and has two projections forming electrical contacts,
 wherein said at least one counter electrode is provided adjacent, and on the same side of said common permeable substrate as said at least one sensing electrode.

9. The gas sensor according to claim 1, wherein:
 a shape of said at least one sensing electrode has a recess, and
 wherein said at least one test electrode is located in said recess, separated by a U-shaped channel, said at least one test electrode being located in a center of said sensing electrode, said at least one test electrode having a contact strip extending from said at least one test electrode to an electrical terminal means, said contact strip being insulated from said at least one electrolyte.

10. The gas sensor according to claim 1, further comprising:
 blockage means for preventing flow of gas generated by said test electrode, and thereby forcing said gas generated by said test electrode to flow through said at least one electrolyte to reach said at least one sensing electrode.

11. The gas sensor according to claim 1, further comprising:
 a manifold; and
 a control circuitry,
 wherein said at least one test electrode comprises:
  a first gas generator electrode; and
  a second gas generator electrode,
 wherein said manifold is shared by said first gas generator electrode and said at least one sensing electrode, said manifold allowing a first test gas generated by said first gas generator electrode to reach said at least one sensing electrode therethrough,
 wherein said second gas generator electrode does not share said manifold with said at least one sensing electrode, a second test gas generated by said second gas generator electrodes flowing through said at least one electrolyte to reach said at least one sensing electrode, and
 wherein said control circuitry is operable to control said first gas generator electrode and said second gas generator electrode in accordance with a test sequence.

12. The gas sensor according to claim 1, further comprising:
 a valve means for closing said housing to said environment during a self testing.

13. A gas sensor, comprising:
 a housing having disposed therein:
  at least one sensing electrode;
  at least one counter electrode;
  at least one test electrode; and
  at least one electrolyte in contact with at least one of said at least one sensing electrode, said at least one counter electrode and said at least one test electrode;
 wherein said housing permits at least a gas to be sensed to flow from an environment to said at least one sensing electrode;

wherein said gas sensor is operable in a normal mode of operation in which said gas sensor detects whether said gas to be sensed is present at said at least one sensing electrode, and in a test mode of operation in which said at least one test electrode generates a test gas which flows to said at least one sensing electrode to enable an indication whether said gas sensor is operating correctly;

wherein at least two of said at least one sensing electrode, said at least one counter electrode and said at least one test electrode are mounted side-by-side on a same side of a common porous gas permeable substrate to define a planar electrode assembly; and wherein said at least one sensing electrode and said at least one test electrode are mounted side-by-side on the same side of said common porous gas permeable substrate and are in contact with separate electrolytes.

14. The gas sensor according to claim 13, further comprising:

at least one reference electrode.

15. The gas sensor according to claim 14, wherein:

said at least one counter electrode, said at least one sensing electrode, said at least one reference electrode, and said at least one test electrode are mounted side-by-side on the same side of the common porous gas permeable substrate.

16. The gas sensor according to claim 14, comprising:

at least two counter electrodes.

* * * * *